(12) United States Patent
McGann et al.

(10) Patent No.: US 7,338,638 B2
(45) Date of Patent: Mar. 4, 2008

(54) TRAPPING MATERIALS FOR TRACE DETECTION SYSTEMS

(75) Inventors: William J. McGann, Raynham, MA (US); Kevin J. Perry, Pelham, NH (US); Sherry L. Lepine, Bedford, NH (US)

(73) Assignee: GE Homeland Protection, Inc., Newark, CA (US)

( * ) Notice: Subject to any disclaimer, the term of this patent is extended or adjusted under 35 U.S.C. 154(b) by 668 days.

(21) Appl. No.: 10/640,551

(22) Filed: Aug. 13, 2003

(65) Prior Publication Data

US 2004/0131503 A1    Jul. 8, 2004

Related U.S. Application Data

(60) Provisional application No. 60/404,556, filed on Aug. 19, 2002.

(51) Int. Cl.
    *G01N 30/00*    (2006.01)
(52) U.S. Cl. .......................... 422/78; 422/88; 436/110; 73/863.22; 73/28.01
(58) Field of Classification Search ................. 422/78, 422/88; 73/863.22, 28.01, 28.04; 436/110
    See application file for complete search history.

(56) References Cited

U.S. PATENT DOCUMENTS

| 3,699,333 A | 10/1972 | Cohen et al. |
| 4,390,784 A | 6/1983 | Browning et al. |
| 4,772,794 A | 9/1988 | Jenkins |
| 4,818,869 A | 4/1989 | Weber-Grabau |
| 4,855,595 A | 8/1989 | Blanchard |
| 5,027,643 A | 7/1991 | Jenkins |
| 5,200,614 A | 4/1993 | Jenkins |
| 5,291,017 A | 3/1994 | Wang et al. |
| 5,420,424 A | 5/1995 | Carnahan et al. |
| 5,491,337 A | 2/1996 | Jenkins et al. |
| 5,983,732 A * | 11/1999 | Hering et al. ............ 73/863.22 |
| 6,073,499 A | 6/2000 | Settles |
| 6,559,094 B1 * | 5/2003 | Korotkikh et al. .......... 502/326 |

FOREIGN PATENT DOCUMENTS

EP    0 921 210 A1    6/1999

* cited by examiner

*Primary Examiner*—Jill Warden
*Assistant Examiner*—Samuel P Siefke
(74) *Attorney, Agent, or Firm*—GE Global Patent Operation; Jonathan E. Thomas

(57) ABSTRACT

The invention is directed to a trap material use in a chemical trace detection portal for detecting trace amounts of contraband, and more particularly for detecting vapors and particles emitted from drugs and explosive devices. The trap material is made of a metallic foam material, such as aluminum foam metal, copper foam metal, stainless steel foam metal, or a silica-carbon foam metal, which have high thermoconductivity and reduced density, as compared to conventional trap materials, thereby ensuring that the internal temperature of the subject trap rapidly achieves the temperature required during desorbing of the trace materials.

4 Claims, 5 Drawing Sheets

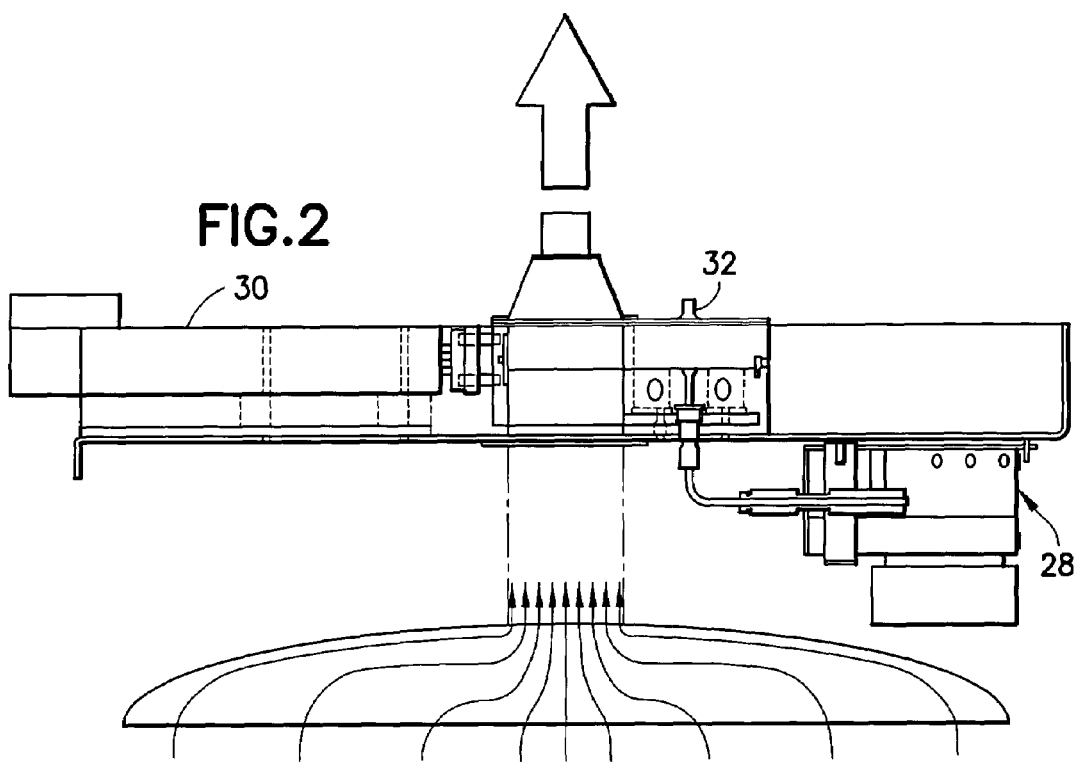
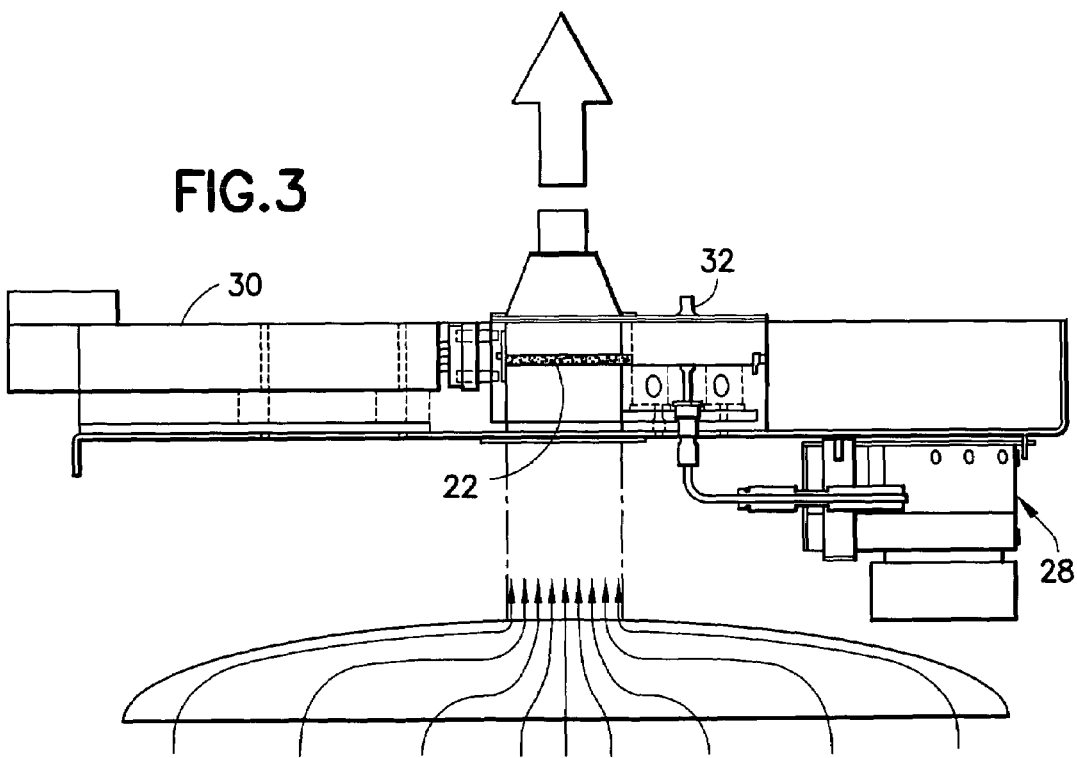

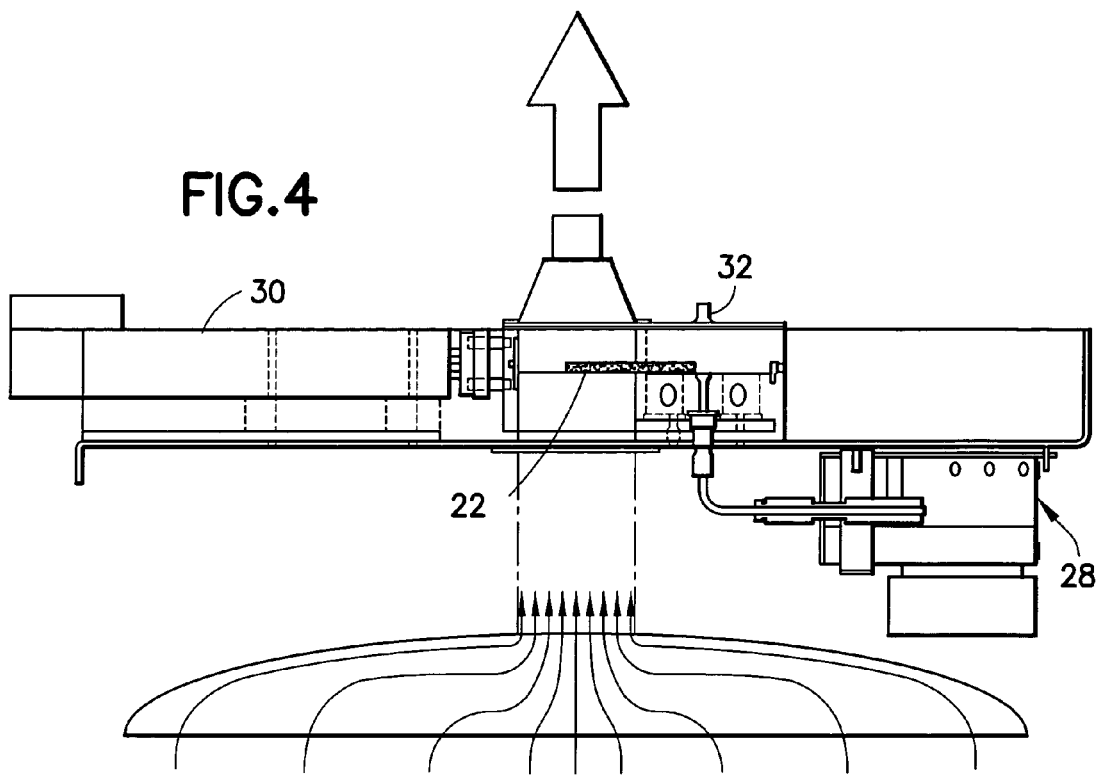
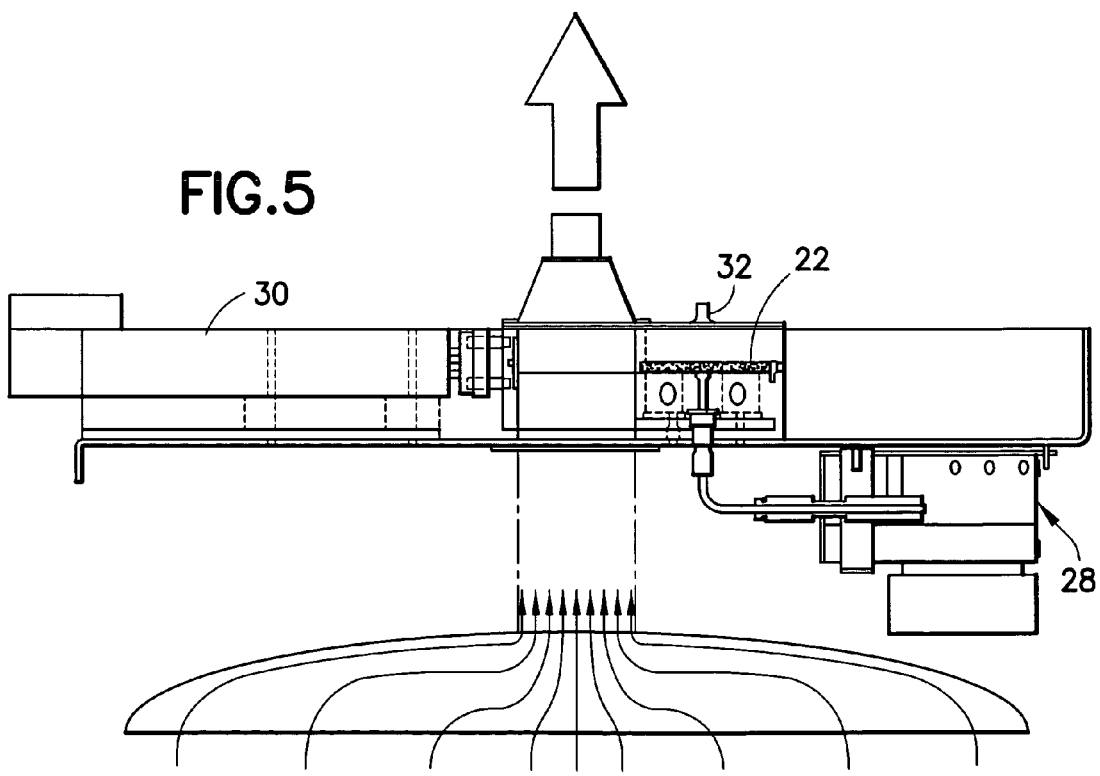

TRAPPING MATERIALS FOR TRACE DETECTION SYSTEMS

This application is a non-provisional of U.S. Provisional Patent Appl. No. 60/404,556 filed Aug. 19, 2002.

BACKGROUND OF THE INVENTION

1. Field of the Invention

A trap material is provided for use in a chemical trace detection portal for detecting trace amounts of contraband. The trap material is made of aluminum foam metal which has a high thermoconductivity and reduced density as compared to conventional trap materials, thereby ensuring that the internal temperature of the improved trap rapidly achieves the temperature required during desorbing of the trace materials.

2. Description of Related Art

Atmospheres have been sampled for the presence of targeted substances for many decades. In particular, the requirement to detect vapors and particles emitted from contraband materials has led to many improvements in sample harvesting and pre-concentration. As an example, reference is made to U.S. Pat. No. 4,242,107 which issued to Anthony Jenkins on Dec. 30, 1980 and is entitled "Apparatus for the Separation of a Constituent From an Atmosphere." In U.S. Pat. No. 4,242,107 there is disclosed an apparatus for sampling an atmosphere for the presence of a constituent in which a flow of the atmosphere is first drawn through a trap capable of releasably absorbing the constituent and the trap is then passed through a carrier gas stream which removes and conveys the constituent into a detector. The trap may comprise a rotatable disc of wire mesh which cuts continuously across a flow of the atmosphere and a carrier gas flow. The volume flow rate of the atmosphere is greater than that of the carrier gas thereby giving a large concentration gain of the constituent in the carrier flow. The apparatus can be used for detecting the presence in the atmosphere of vapors emanating from explosives and for this purpose the carrier gas flow can be directed into an electron capture detector.

The characteristics which are essential for good trap design are: (1) the trap must allow a high flow of air through the material; (2) the trap must trap small particles at the micron level; (3) the trap must have high surface area to trap low volatility vapors; (4) the trap must be strong enough to maintain the pressure drop across the trap necessary to support the high flow requirements; (5) the trap must allow heating to temperatures in excess of 200° C.; and (6) the trap must have a low volume so that the trap can be purged by the low carrier flow within a short time, usually less than one second.

Various materials have been used in the past for the collection and detection of explosives and illicit drugs. Metal gauzes, metal felt blanket, paper, and artificial fiber felts are among the materials that have previously been employed for this purpose.

A new challenge has recently been imposed on top of the already challenging requirements of detecting drugs and explosives in large volumes of air. This is provided by the need to rapidly detect explosives and narcotics on passengers traveling through airport security checkpoints.

U.S. Pat. No. 6,073,499, which issued to Gary S. Settles on Jun. 13, 2000 and is entitled "Chemical Trace Detection Portal Based on the Natural Air Flow and Heat Transfer of the Human Body" discloses a portal provided for use with a detector for detecting trace amounts of contraband that may be retained on skin or clothing of the human subject.

The portal disclosed in U.S. Pat. No. 6,073,499, relies upon the continuous process by which microscopic flakes of skin continuously separate from human subjects. The portal further relies on the existence of a human thermal plume consisting of a layer of warm air adjacent to all human subjects. The warm air rises in the cooler surrounding air and transports the microscopic flakes of skin upwardly. The portal capitalizes on this phenomenon by providing at least a partial enclosure with a funnel-shaped collector above the human subject. A low speed fan of relatively dense cool air may be introduced into the portal to buoyantly lift the warmer air of the human thermal plume upwardly. The air stream defined by the human thermal plume and the skin particles thereof moves to a trap in the funnel-shaped collector of the portal. The trap cooperates with a detector for detecting the presence of molecules of interest.

In a portal system, as disclosed in U.S. Pat. No. 6,073,499, the trap must be heated very rapidly to temperatures of about 200° C. in order to desorb and volatize the trap material. The speed at which this can be achieved is critical to the success of the test, since delays at the checkpoint cannot be accommodated in many airports.

SUMMARY OF THE INVENTION

The present invention addresses the requirement to trap the materials of interest from high flow of air, and then move the trap to a desorber where the trap is heated very rapidly under low flow conditions. Also, when the trap is removed from the desorber, it must be caused to cool down very rapidly so the airborne vapors can again be trapped. The need for a more rapid heat up and cool down pose new demands on the trap material which were not previously considered.

The improved trap material of the subject invention has been preferably developed from aluminum foam metal. Aluminum has much higher thermoconductivity and much lower density than other materials, and this ensures that the internal temperature of the trap rapidly achieves the temperature of the surface. The aluminum foam metal has a much lower density than aluminum itself and requires even less heat to increase the temperature of the trap. The material comprises a continuously connected "open celled" geometry which insures good thermoconductivity and very rapid warm up in the desorbers.

BRIEF DESCRIPTION OF THE DRAWINGS

FIG. 2 is a cross-sectional view of the sample collection system design in the portal of FIG. 1.

FIG. 3 illustrates the sample collection system, with the trap being disposed in the funnel-shaped collector of the portal.

FIG. 4 illustrates the sample collection system during the time when the trap is being moved laterally into the desorber.

FIG. 5 illustrates the sample collection system at which time the trap has been fully indexed into the desorber.

DETAILED DESCRIPTION OF THE PREFERRED EMBODIMENTS

Figure 1:
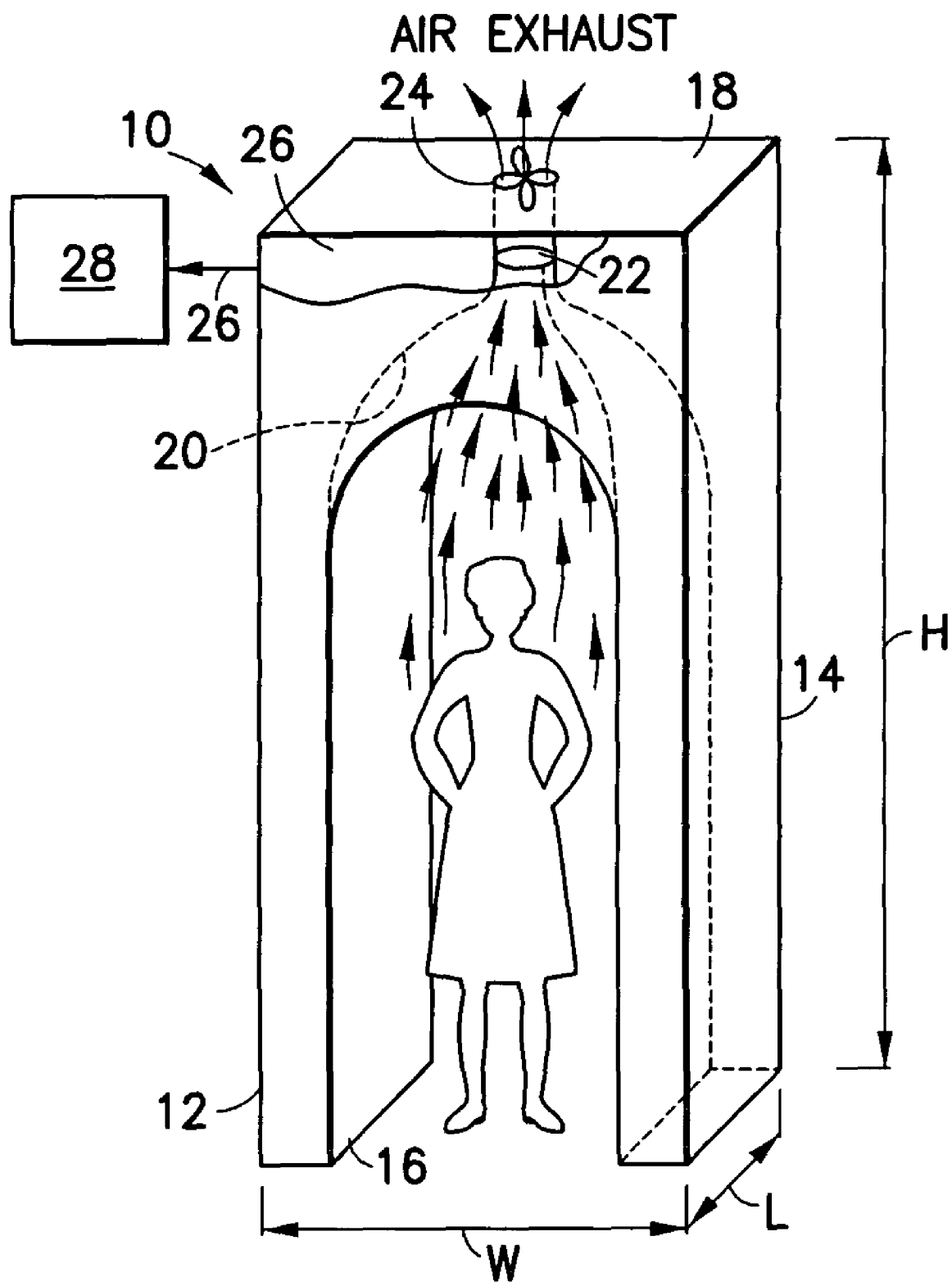
FIG. 1 is a perspective view of a portal-explosives vapor detection system as disclosed in U.S. Pat. No. 6,073,499.

The trap of the subject invention is employed in a portal-explosives vapor detection system as generally illustrated in FIG. 1, and corresponds to the system described in U.S. Pat. No. 6,073,499, the specification of which is incorporated herein by reference.

As illustrated in FIG. 1, the portal 10 has two substantially vertical side walls 12 and 14 that are spaced sufficiently from one another to form an open passage 16 through which a human subject may conveniently pass. Preferably, the side walls are spaced from one another to define an overall width "W" of approximately three feet. Additionally, the side walls 12 and 14 define an overall length "L" of three feet. The portal 10 further has a ceiling 18, which is disposed above the floor or supporting surface for the portal 10 by a distance sufficient to define an overall portal height "H" between approximately seven to ten feet. These dimensions enable most human subjects to pass easily through passage 16 of the portal 10.

Portions of the ceiling 18 that cover the open passage 16 define an inverted, contoured funnel 20 that gradually tapers to smaller cross-sectional dimensions at locations further above the passage 16. The funnel 20 is operative to collect the rising thermal plume generated by the human body. The smaller cross-sectional portions of the funnel 20 are provided with a trap, generally designated by the numeral 22.

The function of the trap 22 is to extract from the human thermal plume a sample of particulates, such as skin flakes with adsorbed compounds thereon or airborne trace chemical in vapor form.

A fan 24 is provided to generate an airflow that will direct the human thermal plume through the trap 22. The air drawn through the fan 24 then is expelled to the environment. A conveyor 26 is further provided to present the trap 22 to a substance detector 28 which is schematically illustrated in FIG. 1. The substance detector 28 may be a prior art detector, such as one of the highly effective detectors disclosed in U.S. Pat. No. 5,200,614 or U.S. Pat. No. 5,491,337.

As illustrated in FIG. 2, sample air is passed through the portal and exhausted. Disposed to one side of the sample trap is the sample desorber and detector 28 while on the other side of the sample trap is a linear actuator 30.

FIGS. 3 through 6 depict, in sequence, the operation of the sample collection system design.

As shown in FIG. 3, the trap is designated by the numeral 22, and warm air is drawn upwardly at a rate of approximately 30 liters per second and the particles are entrapped in the trap 22.

After a designated period, shown in FIG. 4, the linear actuator 30 is actuated to laterally shift the trap 22 into the sample desorber 28.

In FIG. 5, the lateral shifting of the trap 22 is fully complete, during which time the trap is totally within the sample desorber 28. The sample desorber is heated for facilitating the removal of particles, including condensed vapor, from the trap and clean air is injected at low speed flow rate into the filter desorber through an inlet designated by the numeral 32. The inlet 32 is shown in the center of the top side of the desorber.

Figure 6:
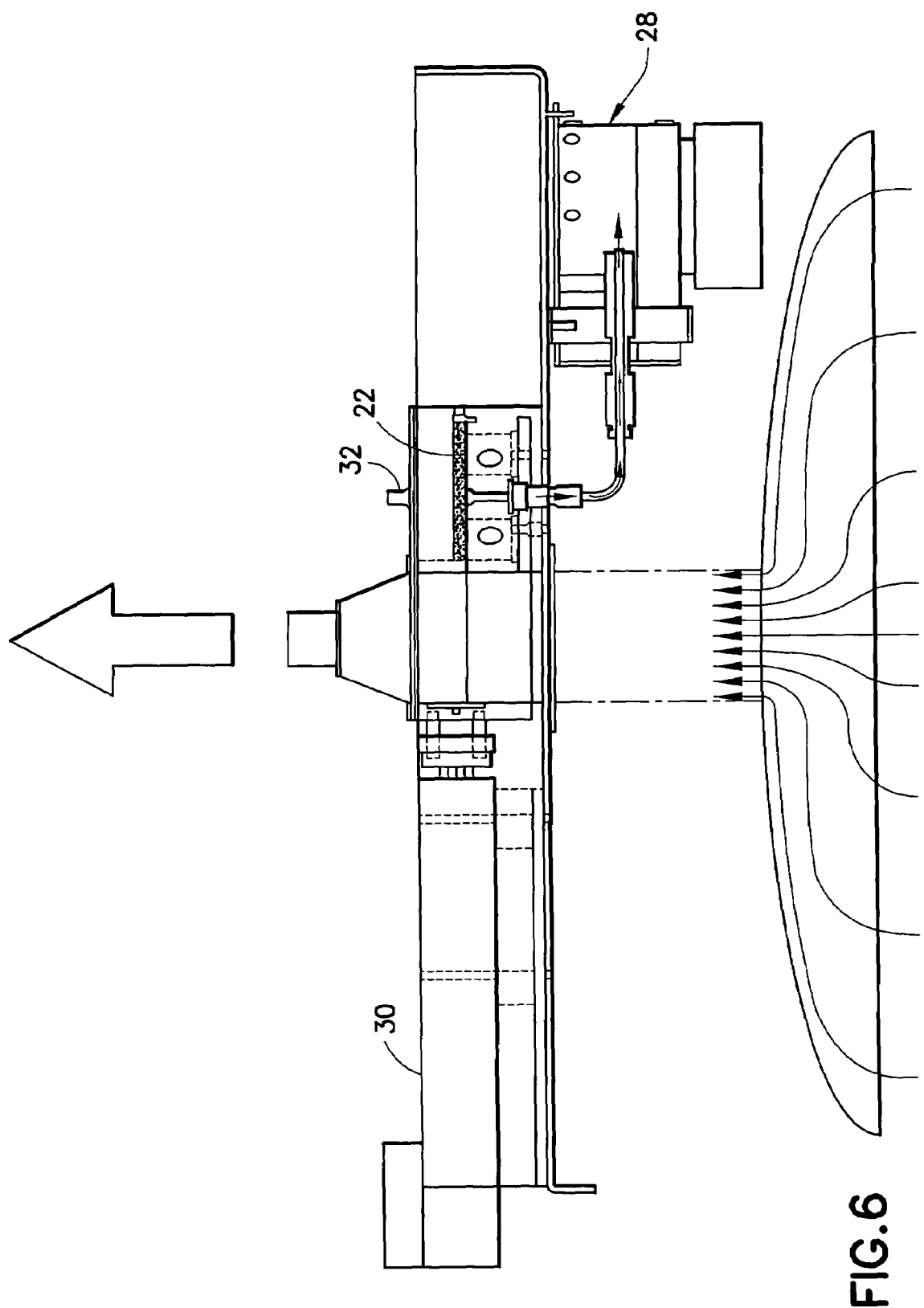
FIG. 6 illustrates the sample collection system at which time the carrier gas is passed through the trap and then to the detector.

At the same time, as shown by the arrows 34 in FIG. 6, a suction is applied to the lower side of the sample desorber in order to draw the clean air and the particles on the filter in to the detector 28. The detector then detects the presence of molecules of interest.

Figure 7:
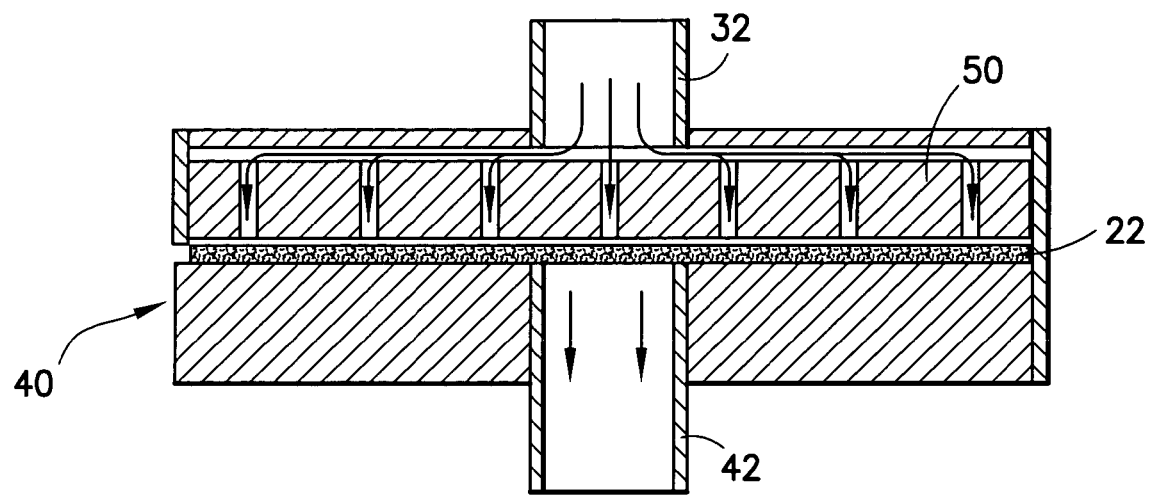
FIG. 7 is a cross-sectional view of the sample desorber with the trap disposed in the desorber.

FIG. 7 schematically illustrates in greater detail and in cross-section the internal structure of the sample desorber. Shown in the cross-sectional view of FIG. 7, the sample desorber is an enclosure having an opening 40 along one side for receiving the trap 22, with the inlet 32 being in communication with the sample desorber at the upper portion thereof, while the outlet 42 leading to the detector is disposed on the opposite lower surface of the sample desorber.

Figure 8:
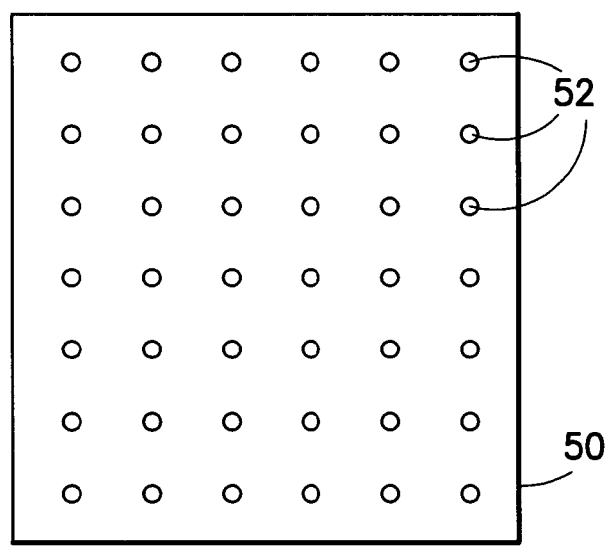
FIG. 8 is a plan view of the manifold plate disposed in the sample desorber.

Disposed within the upper surface of the trap and the top plate of the sample desorber is a manifold plate 50 which, as shown in FIG. 8, has a matrix of spaced holes designated by the numeral 52.

As noted above, the sample desorber is heated in order to facilitate removal of the particles or vapors from the trap. By virtue of the construction of the sample desorber, clean air is input through the inlet 32, and at the same time a vacuum is created at outlet 42, the clean air passes vertically through the manifold and then passes perpendicularly thorough the trap, through the outlet 42 and then to the detector.

The walls of the desorber are formed from substantial, thick metallic members which effectively act as an infinite source of heat when the trap is inserted into the desorber. The temperature of the desorber is held constant at a high temperature, e.g. 200° C. When the trap is inserted, there is a small, but finite, gap between the trap and the desorber in a wall. Heat is transferred to the trap largely by conduction through the air gap (as opposed to radiation and convection).

Hot air is flowed through the manifold and then through the trap itself. This also provides heat to the trap, but since the low flow of air has little thermal inertia, only a small amount of heat is transferred this way. As heat is conducted, the temperature of the trap rises to the temperature of the desorber. The temperature of the inner part of the trap rises more slowly, however.

The speed at which this happens is critical to the success of the test on two counts. The first is the obvious one of passenger delay, and secondly, it is critical that all the material is desorbed very quickly so that the material of interest is desorbed into as small a volume as possible, thus insuring high concentration in the carrier flow entering the detector.

The subject invention relates to new materials which facilitate a trapping process and a fast heat-up/cool-down cycle. The trap made according to the subject invention has the following optimal characteristics: (1) low thermal inertia (mass x specific heat); (2) high conductivity; (3) high surface area; (4) low impedance to flow; and (5) good trapping efficiency for micron-sized particles.

Prior art traps have only considered parameters 3, 4, and 5 noted above. One previously employed trap material was stainless steel felt blanket. This has a high surface area and good trapping efficiency for micron-sized particles. Unfortunately, stainless steel felt blanket has both high thermal inertia and low thermal conductivity.

In another prior art design, the trap takes several seconds to achieve sufficiently high temperature to desorb plastic explosives or some of the less volatile illicit drugs. In the reverse direction, the prior art trap is moved into the sample air stream, but remains hot until the action of the high sampled air flow causes the trap to cool down. During the cooling period, volatile materials such as dynamite vapor or the vapor methamphetamine will not be trapped in the hot trap.

The preferred trap material of the subject invention has been developed from aluminum foam metal. Aluminum has much higher thermoconductivity and much lower density than stainless steel, which insures that the internal temperature of the trap rapidly achieves the temperature of the surface. The aluminum foam metal has much lower density than aluminum itself and requires even less heat to increase the temperature of the trap. The aluminum foam metal trap comprises a continuously connected, open celled geometry which insures good thermoconductivity and very rapid warm-up in the desorber.

Aluminum foam metal traps may be fabricated in thicknesses ranging from 2 to 10 mm. The metal foaming process produces panels typically about 10 mm and greater, but this is larger than optimal for the low dead volume requirements in the desorber. Thin panels of about 2 mm thick have been successfully made by compressing the foam metal in a press or roller. Resulting traps have a density of between 10% and 15% of the density of the parent aluminum.

Aluminum foam metal may be obtained from ERG Materials and Aerospace Corporation of Oakland, Calif. DUOCEL is the descriptive name given to a wide variety of materials including aluminum foam metal. These materials exhibit a continuously connected, open-celled (reticulated) geometry having a duodecahedronal cell shape. DUOCEL aluminum foam metal is available in a density range of 3% to 50% relative to the solid base metal and a cell density of 5, 10, 20 and 40 pores per linear inch, with material density and cell size independently variable. DUOCEL is presently available in aluminum alloy 6101 and A356, with other alloys available on special order.

DOUCEL is a true metal skeletal structure. It is not a sintered, coated, or plated product. Its purity is typically that of the parent alloy metal, with no voids, inclusions, or entrapments. DOUCEL is manufactured by directional solidification of metal from a super-heated liquidus state in an environment of overpressures and high vacuum. The resulting material has a reticulated structure of open, duodecahedronal-shaped cells connected by continuous, solid metal ligaments. The solid-metal ligaments routinely test to 99 percent purity of the parent alloy (to AMS specifications), are not porous, and approximate single strand drawn wire.

The matrix of cells and ligaments in the metal skeletal structure is completely repeatable, regular, and uniform throughout the entirely of the material. DUOCEL is a rigid, highly porous and permeable structure and has a controlled density of metal per unit volume.

The density of metal and cell size (expressed as pores per inch) can each be varied independently to tailor the properties of the material to meet specific design requirements. Density is continuously variable from 3 percent to 12 percent. Cell size can be 5, 10, 20, or 40 pores per inch (ppi). (Mean cell sizes of 0.170", 0.080", 0.040", or 0.020".)

Besides aluminum foam material, the trap of the subject invention may also be made of a copper foam metal; a stainless steel foam metal; or a silica-carbide foam metal.

Since the foregoing descriptions and drawings are merely illustrative, the scope of protection of the invention has been more broadly stated in the following claims; and these should be liberally interpreted so as to obtain the benefit of all equivalents to which the invention is fairly entitled.

What is claimed is:

1. An apparatus for testing whether an object contains a substance of interest, said apparatus comprising:
   a testing station for receiving the object to be tested;
   a trap formed from a silica-carbon foam metal having a reticulated open cell structure and disposed for receiving a flow of air from the testing station;
   a heater for heating the foamed metal trap sufficiently to volatize material on the trap;
   an air pump for generating a flow of air across the trap; and
   a detector for receiving the flow of air across the trap and for testing whether the flow of air across the trap contains any of the particles of interest.

2. The apparatus of claim 1, wherein the trap has a thickness of less than 10 mm.

3. The apparatus of claim 1, wherein the trap has a thickness of approximately 2 mm.

4. The apparatus of claim 1, wherein the detector is an ion trap mobility spectrometer.

* * * * *